(12) United States Patent
Bayer et al.

(10) Patent No.: US 8,337,936 B2
(45) Date of Patent: Dec. 25, 2012

(54) IMPLANT AND METHOD FOR MANUFACTURING SAME

(75) Inventors: Ullrich Bayer, Admannshagen-Bargeshagen (DE); Jan Schettler, Rostock (DE); Guenter Ewert, Rostock (DE)

(73) Assignee: Biotronik VI Patent AG, Baar (CH)

( * ) Notice: Subject to any disclaimer, the term of this patent is extended or adjusted under 35 U.S.C. 154(b) by 483 days.

(21) Appl. No.: 12/564,282

(22) Filed: Sep. 22, 2009

(65) Prior Publication Data

US 2010/0087914 A1    Apr. 8, 2010

(30) Foreign Application Priority Data

Oct. 6, 2008  (DE) .................. 10 2008 042 602

(51) Int. Cl.
  *B05D 3/10* (2006.01)
  *C25D 5/18* (2006.01)
  *C25D 11/18* (2006.01)
  *C25D 11/02* (2006.01)
  *C25D 9/06* (2006.01)

(52) U.S. Cl. ....... 427/2.1; 427/2.24; 427/2.25; 427/331; 427/337; 205/107; 205/318; 205/322; 205/324; 205/203

(58) Field of Classification Search .......... 427/2.1–2.31, 427/569, 570, 576, 331, 337; 205/108, 107, 205/318, 322, 324

See application file for complete search history.

(56) References Cited

U.S. PATENT DOCUMENTS

| | | | | | |
|---|---|---|---|---|---|
| 484,637 | A | * | 10/1892 | Hunter | 219/155 |
| 5,354,390 | A | * | 10/1994 | Haszmann et al. | 148/518 |
| 5,824,651 | A | * | 10/1998 | Nanci et al. | 427/2.26 |
| 5,847,825 | A | * | 12/1998 | Alexander | 356/318 |
| 6,527,938 | B2 | * | 3/2003 | Bales et al. | 205/229 |
| 6,919,012 | B1 | * | 7/2005 | Bucar | 205/107 |
| 7,488,343 | B2 | * | 2/2009 | O'Brien et al. | 623/1.15 |
| 7,901,726 | B2 | * | 3/2011 | McMorrow et al. | 427/2.1 |
| 2003/0188972 | A1 | * | 10/2003 | Shatrov et al. | 205/91 |

(Continued)

FOREIGN PATENT DOCUMENTS

DE     43 03 575 C1     4/1994

(Continued)

OTHER PUBLICATIONS

Gunzel et al. Corrosion protection of titanium by deposition of niobium thin films.Surface and Coatings Technology 116-119 (1999) 1107-1110.*

(Continued)

*Primary Examiner* — Timothy Meeks
*Assistant Examiner* — Cachet Sellman
(74) *Attorney, Agent, or Firm* — Biotech Beach Law Group PC (57) ABSTRACT

The present invention proposes a method for manufacturing an implant, in particular an intraluminal endoprosthesis, having a body such that the body has metallic material. To control the degradation in a desired time window, e.g., between four weeks and six months, the following production method is performed: a) preparing the body of the implant, and b) plasma-chemical treatment of at least a portion of the surface of the body in an aqueous solution by applying a plasma-generating electric alternating voltage to the body (5) of the implant, said voltage having a frequency of at least approximately 1 kHz, to create a first layer. The invention also relates to an implant obtainable by such a method.

20 Claims, 1 Drawing Sheet

U.S. PATENT DOCUMENTS

| | | |
|---|---|---|
| 2005/0000819 A1 | 1/2005 | LeGeros et al. |
| 2006/0199876 A1* | 9/2006 | Troczynski et al. ........ 523/115 |
| 2006/0229711 A1* | 10/2006 | Yan et al. .................. 623/1.38 |
| 2007/0259101 A1* | 11/2007 | Kleiner et al. .............. 427/2.24 |
| 2008/0047837 A1* | 2/2008 | Birss et al. .................. 205/96 |
| 2008/0081212 A1* | 4/2008 | Inbe et al. .................. 428/651 |
| 2008/0243242 A1* | 10/2008 | Kappelt et al. ............. 623/1.46 |
| 2008/0249600 A1* | 10/2008 | Atanasoska et al. ......... 623/1.4 |
| 2009/0028785 A1* | 1/2009 | Clarke ........................ 424/1.11 |

FOREIGN PATENT DOCUMENTS

| | | |
|---|---|---|
| EP | 1 891 989 A1 | 8/2006 |
| WO | WO 03/083181 A2 | 10/2003 |
| WO | WO 03/094774 A1 | 11/2003 |
| WO | WO 03094774 A1 * | 11/2003 |
| WO | WO 2008/045184 A1 | 4/2008 |
| WO | WO 2008/074175 A2 | 6/2008 |

OTHER PUBLICATIONS

Abedin. A Study of electrodeposition on tantalum on NiTi.Electrochemistry Communications 7 (2005) 941-946.*
Yerokhin et al. Fatigue properties of Keronitecoatings on a magnesium alloy.Surface and Coatings Technology 182 (2004) 78-84.*
German search report for priority application DE 10 2008 042 602.4.

* cited by examiner

IMPLANT AND METHOD FOR MANUFACTURING SAME

CROSS REFERENCE TO RELATED APPLICATIONS

The present invention claims benefit of priority to Germany patent application number DE 10 2008 042 602.4, filed on Oct. 6, 2008, the contents of which are herein incorporated by reference in their entirety.

FIELD OF THE INVENTION

The invention relates to a method for manufacturing an implant, in particular an intraluminal endoprosthesis.

BACKGROUND OF THE INVENTION

Medical endoprostheses or implants for a wide variety of applications are known in large numbers from the prior art. Implants in the sense of the present invention are understood to be endovascular prostheses or other endoprostheses, e.g., stents, fastening elements for bones, e.g., screws, plates or nails, surgical suture materials, intestinal clamps, vascular clips, prostheses in the area of hard and soft tissue as well as anchoring elements for electrodes, in particular pacemakers or defibrillators.

Stents are a type of implant used especially frequently today for treatment of stenoses (vascular occlusions). They have a body in the form of a tubular or hollow cylindrical basic mesh, which is open at each longitudinal end. The tubular basic mesh of such an endoprosthesis is inserted into the vessel to be treated and serves to support the vessel. Stents have become established for treatment of vascular diseases in particular. Through the use of stents, constricted areas in the vessels can be dilated, resulting in an increased lumen. Although an optimum vascular cross section, which is needed primarily for successful treatment, can be achieved by using stents or other implants, the permanent presence of such a foreign body initiates a cascade of microbiological processes, leading to a gradual overgrowth of the stent and in the worst case to a vascular occlusion.

One starting point for solving this problem consists of manufacturing the stent and/or other implants of a biodegradable material.

The term "biodegradation" is understood to refer to hydrolytic, enzymatic and other metabolic degradation processes in a living organism, where these processes are caused mainly by the body fluids coming in contact with the biodegradable material of the implant and leading to a gradual dissolution of the structures of the implant containing the biodegradable material. As a result of this process, the implant loses its mechanical integrity at a certain point in time. The term "biocorrosion" is often used as synonymous with the term "biodegradation." The terms "bioresorption" and "bioabsorption" refer to the subsequent resorption or absorption of the degradation products by the living organism.

Materials suitable for implants that are biodegradable in the body may contain polymers or metals, for example. The basic lattice may consist of several of these materials. What these materials have in common is their biodegradability. Examples of suitable polymer compounds include the polymers from the group comprising cellulose, collagen, albumin, casein, polysaccharides (PSAC), polylactide (PLA), poly-L-lactide (PLLA), polyglycol (PGA), poly-D,L-lactide-co-glycolide (PDLLA-PGA), polyhydroxybutyric acid (PHB), polyhydroxyvaleric acid (PHV), polyalkyl carbonates, polyorthoesters, polyethylene terephtalate (PET), polymalonic acid (PML), polyanhydrides, polyphosphazenes, polyamino acids and their copolymers as well as hyaluronic acid. Depending on the desired properties, the polymers may be present in pure form, in derivatized form, in the form of blends or as copolymers. Biodegradable metallic materials are based on alloys of magnesium and/or iron.

Stents which have coatings with various functions are already known. Such coatings are used, for example, to release medications, to arrange an X-ray marker or to protect the underlying structures.

In the implementation of biodegradable implants, the degradability should be controlled in accordance with the desired treatment and/or use of the respective implant (coronary, intracranial, renal, etc.). For many therapeutic applications, for example, an important target corridor is that the implant must lose its integrity within a period of four weeks to six months. The term "integrity," i.e., mechanical integrity, is understood to refer to the property whereby the implant has hardly any mechanical losses in comparison with the undegraded implant. This means that the implant still has enough mechanical stability that the collapse pressure, for example, has declined only slightly, i.e., at most to 80% of the nominal value. The implant may thus retain its main function, namely keeping the blood vessel open, while retaining its integrity. Alternatively, the integrity may be defined as meaning that the implant is still mechanically stable to such an extent that it is hardly subject to any geometric changes in its stress state in the vessel; for example, it does not collapse to any significant extent, i.e., it still has at least 80% of the dilatation diameter under stress or, in the case of a stent, hardly any of the load-bearing struts are broken.

Biodegradable magnesium implants, in particular magnesium stents, have proven to be especially promising for the aforementioned target corridor of degradation, but they lose their mechanical integrity and/or supporting effect too soon on the one hand, while on the other hand, the loss of integrity fluctuates greatly in vitro and in vivo. This means that in the case of magnesium stents, the collapse pressure declines too rapidly over time and/or the reduction in the collapse pressure has an excessively greatly variability and therefore cannot be determined.

Various mechanisms of controlling the degradation of magnesium implants have already been described in the prior art. For example, these are based on organic and inorganic protective layers or combinations thereof, which present a resistance to the human corrosion medium and the corrosion processes taking place there. Approaches to solving this problem known in the past have been characterized in that harrier layer effects are achieved, based on a spatial separation, preferably free of defects, between the corrosion medium and the metallic material, in particular the metallic magnesium. The degradation preventing effect is secured by protective layers having various compositions and by defined geometric distances (diffusion barriers) between the corrosion medium and the magnesium base material. Other approaches have been based on alloy components of the biodegradable material of the implant body, which influence the corrosion process by displacement of the layer in the electrochemical voltage series. Other approaches in the field of controlled degradation induce intended breaking effects by applying physical changes (e.g., local changes in cross section) and/or chemical changes in the stent surface (e.g., multilayers having different chemical compositions locally). However, with the approaches mentioned so far, it is usually impossible to make the dissolution that occurs as a result of the degradation process and its resulting breakage of the stents occur in the required time window. The result is that degradation of the implant begins either too early or too late or there is too much variability in the degradation.

Another problem in conjunction with coatings is derived from the fact that stents or other implants usually assume two states, namely a compressed state with a small diameter and an expanded state with a larger diameter. In the compressed state, the implant can be inserted by means of a catheter into the blood vessel to be stented and positioned at the site to be treated. At the site of treatment, the implant is then dilated by means of a balloon catheter, for example, and/or (when using a memory alloy as the implant material) converted to the expanded state by heating to a temperature above a critical temperature. Because of this change in diameter, the body of the implant is exposed to a mechanical stress in this process. Additional mechanical stresses on the implant may occur during production or in movement of the implant in or with the blood vessel in which the implant is inserted. With the known coatings, this yields the disadvantage that the coating cracks during deformation of the implant (e.g., forming microcracks) or is also removed to some extent. This may result in an unspecified local degradation. Furthermore, the onset and the rate of degradation depend on the size of the microcracks formed due to deformation and their distribution, these microcracks being defects that are difficult to monitor. This leads to a great deal of scattering in the degradation times.

The document DE 10 2006 060 501 describes a method for manufacturing a corrosion-inhibiting coating on an implant made of a biocorrodible magnesium alloy and an implant obtainable by this method, in which, after providing the implant, the implant surface is treated with an aqueous or alcoholic conversion solution containing one or more ions selected from the group $K^+$, $Na^+$, $NH_4^-$, $Ca^{2+}$, $Mg^{2+}$, $Zn^{2-}$, $Ti^{4+}$, $Zr^{4+}$, $Ce^{3+}$, $Ce^{4+}$, $PO_3^{3-}$, $PO_4^{3-}$, $HPO_4^{2-}$, $H_2PO_4^-$, $OH^-$, $BO_3^{3-}$, $B_4O_7^{3-}$, $SiO_3^{2-}$, $MnO_4^{2-}$, $MnO_4^-$, $VO_3^-$, $WO_4^{2-}$, $MoO_4^{2-}$, $TiO_3^{2-}$, $Se^{2-}$, $ZrO_3^{2-}$ and $NbO_4^-$, where a concentration of the ion(s) in the range of $10^-$ mol/L to 2 mol/L prevails. The treatment of the implant surface with the aforementioned conversion solution necessitates anodic oxidation of the implant. It is performed either with or without using an external current source (externally currentless). However, the examples of processes and electrolyte compositions described in this publication do not fulfill expectations about the degradation behavior and dilatation ability without destruction of the layer during use in the case of a magnesium stent.

A medical device such as a catheter or stent is known from the documents US 2008/0086195 A1 and WO 2008/045184 A1 in which a polymer-free coating is applied by means of a plasma electrolytic process plasma electrolytic deposition (PED). The plasma electrolytic coating is used to introduce additional active ingredients containing a medication or a therapeutic agent into the coating. The plasma electrolytic coating comprises a plasma electrolytic oxidation (PEO), a micro-arc oxidation (MAO), a plasma arc oxidation (PAO), an anodic spark oxidation and plasma electrolytic saturation (PES). The plasma electrolytic coating is performed by means of pulsed alternating voltage or direct voltage at voltages between $-100$ V and $600$ V. The current densities vary in the range from 0.5 to 30 $A/dm^2$. A range of 10 to 100 Hz is given in these documents as a suitable a.c. voltage frequency range for the disclosed application. The plasma electrolytic treatment includes the use of various electric potentials between the medical device and a counter-electrode, which generates an electric discharge (a spark discharge or a micro-arc plasma discharge) at or in the vicinity of the surface of the medical device. The method characterized in the documents cited thus does not solve the problem defined above.

SUMMARY OF THE INVENTION

Consequently, the object of the present invention is to provide a method for manufacturing an implant, which will allow degradation of the implant in the desired target corridor. The degradation should take place at a controllable point in time and should allow dilatation and/or deformation of the implant without any mentionable influence on the degradation behavior. Accordingly, the object of the invention also includes creating such an implant.

The above object is achieved by a method comprising the following steps:
a) preparing the body of the implant,
b) plasma-chemical treatment of at least a portion of the surface of the body in an aqueous solution by applying an electric alternating voltage generating the plasma to the body of the implant, said voltage having a frequency of at least approximately 1 kHz to generate a first layer on the treated part of the surface of the body.

In another aspect of the present invention an implant and in particular an intraluminal endoprosthesis, is provided having a body which has at least one metallic material, obtained by the methods of the present invention, wherein the thickness of the first layer created by the plasma-chemical treatment on the surface of the body is approximately 1 μm to approximately 20 μm.

DETAILED DESCRIPTION OF THE INVENTION

The present invention comprises the treatment of the surface of the body in an aqueous electrolyte system (aqueous solution) in which plasma-chemical effects occur directly on the to surface of the body of the implant. The plasma at the surface of the body is stable for a few microseconds and creates reaction products that lead to the development of the first layer on the surface of the body. The body of the implant here comprises at least a portion of the implant, preferably most of the implant, which produces the mechanical integrity of the implant.

The advantage of the inventive method is that oxides and hydroxides of the metallic material are formed due to the plasma-chemical treatment on the surface of the body of the implant. This layer composition provides temporary protection from corrosion in contact with body fluid, causing delayed degradation of the metallic material. The particles released in the wake of the delayed degradation of the implant are partially incorporated by endogenous cells and/or further degraded. The degradation-inhibiting layer produced by the inventive method has pores due to the process which initially of course form weak points due to corrosion through which contact with the metallic base material is facilitated for the electrolyte. However, the surface analytical investigations conducted before and after the degradation tests have shown that the formation of hydroxide associated with the plasma-chemical treatment leads to a locally limited sealing of the base of the pores.

Sealing of the base of the pores may be demonstrated, for example, on the basis of the multi-step changes in the pH of the electrolyte in a corrosion test (for example, in synthetic plasma). In the first seven days, the pH rises from 7.4 to 8.5 to 8.7, as expected. After a change in media performed after seven days, the pH surprisingly rises from 7.4 to only 8.0. This method shows a lower chemical activity of the metallic base material (in particular the magnesium) with the corrosive medium. This effect is associated with stopping the reduction in cross section of the material of the implant body, which is apparent in the metallographic polished section after only seven days. This effect may be explained, for example, as being due to hydroxides of the metallic material filling up the pores in the first layer and thus preventing contact of the electrolyte with the metallic base material. Due to this self-healing effect, the lifetime of the implants under physiological conditions is greatly prolonged. Furthermore, the degradation rate can be controlled by varying the layer thickness. This opens the possibility of adapting the degradation time of the implant to the specific implantation site (coronary, inter-cranial, renal. etc.).

The inventive method is also characterized in that a plasma-generating alternating voltage at a frequency of at least 1 kHz is applied to the body of the implant. This is a high frequency in comparison with the prior art and produces a high energy input into the body and/or the surface of the body of the implant, so the oxides and hydroxides of the metallic material reach comparatively far into the surface of the implant body. The first layer thus adheres very well to the surface of the body.

Based on the anodic principle of action of the plasma-chemical coating, there is no risk of hydrogen embrittlement. There is also no risk of mechanical damage because the surface roughening is not performed mechanically.

The aqueous solution for the plasma-chemical treatment preferably contains phosphate ions, so that in addition to the oxides and hydroxides of the underlying metallic material, phosphates of the body material are also formed in the first layer and ensure a better biocompatibility of the implant material, in particular the coating. The phosphate ions originate from the addition of potassium dihydrogen phosphate and/or dipotassium hydrogen phosphate and/or potassium phosphate and/or sodium dihydrogen phosphate (dihydrate) and/or heptahydrate and/or dodecahydrate to the aqueous electrolytes. The preferred concentration range is between 5 g/L and 200 g/L of the added compound in the aqueous solution. An especially preferred concentration is between 50 g/L and 100 g/L potassium dihydrogen phosphate.

In another preferred exemplary embodiment, the body has at least one metallic material that is at least mostly biodegradable. The treatment of the implant of a biodegradable material by a plasma-chemical method results in temporary corrosion protection when in contact with the body fluid, delaying the degradation of the metallic material.

Another advantage of the inventive method is that surface contamination of the base material, which cannot be removed, is absorbed by the first layer and therefore cannot have any additional influence on the degradation process. Furthermore, this covers any sharp-edged precipitates protruding out of the surface of the implant body (e.g., undissolved components of the alloy). This also leads to an increased hemocompatibility and biocompatibility.

Furthermore, the process-related porous structure of the first layer has a high plastic deformation capacity. For example, the microcracks formed on dilatation of a stent are stopped by energy accumulation and/or dissipation in the pores in the vicinity of the microcracks. Therefore, there is no delamination of the first layer.

Because of the existence of the first layer produced by the inventive method, the storage and shipping conditions for implants manufactured by the inventive method are simplified because the stability of such an implant with respect to degradation is greater than that of uncoated implants.

In a preferred exemplary embodiment, the aqueous solution contains one or more ions of $Sr^{2-}$ which are preferably present in the aqueous solution in a concentration of 0.05 mol/L up to 2.0 mol/L $Sr^{2-}$. This results in strontium compounds being incorporated into the first layer, i.e., the surface layer of the implant. This is advantageous because strontium carbonate in particular has an extremely low solubility in water and thus forms a layer component in the surface layer that has an especially strong inhibiting effect on the degradation. Furthermore, the strontium carbonate present in the coating can manifest a drug-like effect against cerebral sclerosis in cranial applications, for example.

In another especially preferred exemplary embodiment of the present invention, a second layer containing at least one element, preferably two elements from the group consisting of tantalum, niobium, zinc, iron and aluminum, in particular nanocrystalline aluminum, is applied to at least a portion of the surface of the body before the plasma-chemical treatment. Such a coating is used in particular for implant bodies made of materials such as stainless steel 316L, nickel-titanium alloys and cobalt-chromium alloys (e.g., L605).

The materials mentioned above have the disadvantage that they release nickel ions, but the influence of nickel ions on the patient being treated is not considered to be uncritical. The same thing is also true of vanadium ions dissolving out of the alloy TiAl6V4, which is widely used in orthopedics. Such release effects are observed even when diffusion barriers of endogenous or exogenous materials are applied to these materials.

Surface treatment methods that are widely used at the present time for such implants include electropolishing, which creates and/or strengthens the effect of passivation layers, consisting of chromium oxides and/or titanium oxides, for example. However, the extremely smooth surfaces of the implant body due to electropolishing have proven to be a disadvantage, e.g., for adhesion of polymer cover layers which are to be applied subsequently and are to serve as a reservoir for active ingredients and/or drugs. To improve the adhesion, a roughened surface which could be created, e.g., by chemical etching methods (e.g., pickling in acid solutions) would be desirable. However, as a disadvantage, such an etching method would destroy the passivation layer and would increase the risk of oxygen embrittlement.

Another aspect in the production of endoprostheses which includes a desirable embodiment concerns the radiopacity of the implants. This radiopacity is usually achieved by structural changes, e.g., through the incorporation of X-ray markers and/or application of heavy metal layers, preferably radiopaque layers of metal, e.g., gold. However, such a layer leads to a low corrosion resistance of the material composite because local elements are formed. Furthermore, the adhesion of a gold coating is too low.

The inventive approach according to the preferred exemplary embodiment consists of applying a second layer to the surface of the body, in particular in the case of materials of the implant body containing nickel and/or vanadium, before the plasma-chemical treatment, such that the second layer contains at least one element of the group comprising tantalum, niobium, zinc, iron and aluminum, in particular nanocrystalline aluminum. Such a layer composite of a second layer and a first layer above it produced by a plasma-chemical treatment has the advantage that an increased diffusion barrier is created by the metallic tantalum, niobium, zinc, iron and/or aluminum, in particular nanocrystalline aluminum, ensuring biocompatibility for metal ions (Ni, V) that are not biocompatible.

It has also proven to be advantageous that an increased adhesion effect for subsequent degradable or nondegradable polymers or inorganic cover layers is achieved by the surface roughness created by the first layer, such that the inorganic cover layers may serve as drug-releasing vehicle media (active pharmaceutical substance), for example.

Furthermore, the pore structure of the first layer may function as a substance reservoir for active pharmaceutical substances, which can be incorporated as nanoparticles or microparticles and optionally serve as lubricants to reduce the coefficient of friction in the catheter, also as a reservoir for substances that promote bone growth such as calcium phosphates, temporary contrast agents or cell-growth-inhibiting radioactive substances.

The phrase "active pharmaceutical substance" (or active therapeutic substance or therapeutically active substance) in the sense of the present invention is understood to be a plant-based, animal-based or synthetic active ingredient. i.e., drug (medication) or a hormone used in a suitable dosage as a therapeutic agent for influencing states or functions of the body, as a replacement for active ingredients synthesized by the human or animal body, e.g., insulin, and to eliminate disease pathogens, tumors, cancer cells or exogenous substances or to render them harmless. The release of the substance in the environment of the implant has a positive effect on the course of healing or counteracts pathological changes in the tissue as a result of the surgical procedure and serves to render malignant cells harmless in oncology.

Such active pharmaceutical substances have, for example, an anti-inflammatory and/or antiproliferative and/or spasmolytic effect, so that restenoses, inflammations or (vascular) spasms, for example, can be prevented. Such substances may include, for example, one or more substances from the group of active agents such as calcium channel blockers, lipid regulators (e.g. fibrates), immunosuppressants, calcineurin inhibitors (e.g., tacrolimus), antiphlogistics (e.g., cortisone or diclofenac), anti-inflammatories (e.g., imidazoles), antiallergics, oligonucleotides (e.g., dODN), estrogens (e.g., genistein), endothelializing agents (e.g., fibrin), steroids, proteins, hormones, insulins, cytostatics, peptides, vasodilators (e.g., sartans) and the substances having an antiproliferative action, namely the taxols or taxans, preferably paclitaxel or sirolimus.

Improved radiopacity of the implant is also achieved due to the niobium and/or tantalum coating. Under some circumstances. this makes it possible to eliminate the use of a special X-ray marker.

The high-energy input during the plasma-chemical treatment also ensures that the second layer will adhere very well to the body of the implant because most of the arc discharges act so deeply in the body tissue that the second layer is bonded securely at the interface to the surface of the body.

Other advantages of the combination of the first and second layers are as follows:
increased corrosion stability due to avoidance of contact with layer materials containing local elements,
increased surface hardness leading to improved mechanical handling and reduced scratch sensitivity,
increased corrosion stability due to increased abrasion resistance of the implant in contact with other implants (e.g., stent-supported coiling of intercranial aneurysms) or in contact with bones, vessels, tissues or other organs and organ constituents of the patient being treated with the implant (e.g., in the implantation of osteosynthesis implants, e.g., on insertion of nails, screw contacts/plates),
facilitated wettability with polymer solutions, so that technological advantages are achieved when the implant is immersed in or sprayed with polymer solutions, or
facilitating a subsequent sealing of implant surfaces with polymers that can be deposited from the vapor phase.

The second layer is preferably applied by means of an ionic fluid, sputtering, high-rate atomization and/or vapor deposition. The advantage of applying the second layer by means of an ionic fluid consists of the fact that in application of the layer, in particular when using a binary system, micro-alloy effects may occur between the material of the implant body and the applied material. A layer 20 with a thickness of several nanometers up to a few micrometers is formed by the micro-alloy, which is an alloy of the metals contained in the ionic fluid and the material of the implant body, which could not be produced under the usual conditions of melt metallurgy (e.g., due to little or no mutual solubility). The layer combinations may be deposited on the untreated implant as well as on an implant surface that has previously been electrolytically polished. Such a second layer prevents the elution of cytotoxic metal ions out of the implant body, increases the corrosion resistance of the surface even in a highly deformed state and thus allows treatment of highly reactive implant metal surfaces (e.g., of a magnesium alloy) on which an oxide layer or other unwanted surfaces would be formed immediately on coming in contact with air or in electropolishing in contact with temporary, short-lived compounds. Another advantage of the coating by means of an ionic fluid is that the surface produced in this way ensures an increased corrosion resistance even in a greatly deformed state. The surface of the second layer is microstructured and improves the adhesion of a layer above it. In addition, it is advantageous that a second layer produced in this way suppresses diffusion of Ni, Co, V and Cr ions out of the material of the implant body to the cellular tissue in a manner characterized by long-term stability.

The coating is preferably performed by means of an ionic fluid which contains the pyrrolidinum ions that are extremely reaction-resistant. Such an ionic fluid also has sufficient stability to allow deposition of nanocrystalline aluminum in particular.

In another exemplary embodiment, the implant is rinsed in a solvent, preferably distilled $H_2O$, after the plasma-chemical coating and then is dried, preferably at a temperature of at least about 80° C., especially preferably at least about 100° C., such that the drying is preferably performed in a circulating air oven.

In a preferred exemplary embodiment of the inventive method, one or more additional ions selected from the group of carbonates, hydroxides and silicates are additionally present in the aqueous solution used for the plasma-chemical treatment.

To maintain a constant pH in the electrolyte (aqueous solution), a buffer, preferably potassium dihydrogen phosphate and/or sodium dihydrogen phosphate, is present in the aqueous solution.

In another preferred exemplary embodiment, the implant body is treated electrochemically before the plasma-chemical treatment, preferably being electrochemically polished. This removes impurities from the surface of the implant body so that the plasma-chemical treatment is performed on a defined surface. The electropolish may (must but need not necessarily) take place before applying the second layer. It may also take place after application of the second layer but before the plasma-chemical treatment. The freedom from surface contamination which would otherwise lead to poor adhesion of the coating applied by the plasma-chemical method is important. Electropolishing leads to contamination-free cover layers because of the major material erosion effects (depth effect).

The plasma-chemical treatment of the implant body is preferably accomplished by applying a pulsed voltage, preferably a positive voltage to the body, the amplitude of this voltage being in excess of at least about 90 V during most of the period of the treatment, especially preferably at least about 100 V and preferably increasing in the course of the treatment. Due to these high pulsed voltages with a pulse length of preferably max. about 50 microseconds, especially preferably about 5 microseconds, plasmas are generated on the surface of the implant body, lasting for a few microseconds and leading to reaction of the metallic material of the implant body with the electrolyte. Between the voltage pulses there follows a resting phase of preferably about 100 microseconds.

The plasma-chemical process is preferably performed with a current density of at least about 8 $mA/cm^2$, preferably at least about 10 $mA/cm^2$.

In another especially preferred exemplary embodiment, the plasma-chemical treatment is followed by an aftertreatment of the body of the implant in a strongly basic aqueous sodium hydroxide solution to create a third layer. The pH range here is preferably between about 11 and about 13.8, depending on the NaOH concentration. The temperature of the aftertreatment solution is preferably in the range between room temperature and 70° C. The preferred dwell time of the implant body in the sodium hydroxide solution is between 5 sec and 180 sec.

Due to the aftertreatment, the bases of the pores, which are critical from the standpoint of the corrosion resistance and/or permeability, of the first layer created by the plasma-chemical coating are sealed, so that the third layer is present essentially in the bases of the pores. Only the bases of the pores and not the complete pore are sealed by the aftertreatment, so the positive effect of the surface roughened by the plasma-chemical treatment and the associated high adhesion for polymer cover layers are preserved. This achieves an increased corrosion resistance of the implant, leading to degradation and loss of integrity within a time window of 3 to 12 months, which is of interest for many treatments.

The sealing effect of the pore base, which is attributed to the formation of hydroxides (e.g., magnesium hydroxides when the implant body comprises magnesium) achieved in the preferred exemplary embodiment according to the present invention also produces a very advantageous crack-stopping mechanism which occurs due to the difference in the mechanical consistency of the material of the porous cover layer on the one hand and the material of the sealed pore base on the other hand. It is based on the high capacity of the pores to absorb cracking energy.

Microcracks occur, for example, at the moment of dilatation of stents or other implants, when they are stressed beyond their plastification capacity in microscopic regions. These microcracks lead to uncontrolled and therefore unwanted degradation of the base material of the implant body. The cracks occurring in the layer consisting largely of radiopaque oxides, hydroxides and/or phosphates of the base material, created by a plasma-chemical process in the preferred exemplary embodiment, are stopped in the bases of the pores. On the one hand, this is based on the geometry of the pore, which is static per se and thus accumulates cracking energy, and on the other hand, is based on the hydroxide (e.g., magnesium hydroxide) which is situated at the base of the pore and is viscous in comparison with the remaining layer matrix. The hydroxide layer at the base of the pore is advantageously strengthened by the inventive aftertreatment, so that the crack-stopping mechanism described here functions especially effectively. In this way, a high damage tolerance is achieved in mechanical stress, so that the degradation proceeds more uniformly. The aftertreatment is preferably performed concurrently with an ultrasonic treatment and/or injection of argon and/or nitrogen. The third layer, which is formed essentially at the base of the pores of the first layer, has a thickness of a few 10 nm.

Another advantage of the inventive combination of the first and third layers is that there is no formation of bubbles and therefore there is no loss of lumen in advanced degradation due to semipermeability of the layer composite and/or the formation of bubbles is reduced.

In another preferred exemplary embodiment, a fourth layer, preferably containing a polymer, especially preferably consisting at least predominantly of parylene is applied to the first layer and/or to the third layer after the plasma-chemical treatment or after the aftertreatment described above. Preferred layer thicknesses of the parylene layer are between about 0.5 μm and about 10 μm. Due to such a layer combination, the degradation time of the implant can be increased again significantly. The great ability of parylene to permeate into gaps has an advantageous effect, so there is extensive penetration of parylene into the pores of the first and/or third layers down to the base of the pores. The permeation properties for water, chloride-containing solutions and hydrogen, which are characteristic of parylene, in particular parylene N, ensure a controllable degradation behavior of the implant in combination with the underlying surface, which has been created by a plasma-chemical process and optionally sealed at the base of the pores. This is characterized by a uniform slow corrosion process over the cross section of the implant. Furthermore, the parylene layer makes an additional contribution toward preventing or avoiding the progression of a crack under mechanical stress and prevents partial separation of layers.

The term parylene here refers to completely linear, partially crystalline, uncrosslinked aromatic polymers. The various polymers have different properties and can be divided into four basic types, namely parylene C, parylene D, parylene H and parylene F. Parylene N is preferred for use as the fourth layer in the inventive layer composite.

The first layer and/or the third layer arranged beneath the fourth layer lead to a high adhesion power of the fourth layer because of their porous structure, so that a primer treatment, which would otherwise be necessary, is superfluous.

The above statement of object is also achieved by an implant obtainable by an inventive method as described above. Such an implant has the advantages described above in conjunction with the inventive production process.

The first layer created by means of the plasma-chemical treatment preferably has a thickness of about 1 to 20 μm, especially preferably about 1 to 8 μm. A layer with a thickness of about 2 to 5 μm is to be favored because of the higher plastification capacity.

The second layer preferably has a layer thickness between about 0.5 μm and about 15 μm. This preferred layer thickness range is advantageous because, on the one hand, there is a sufficiently large diffusion barrier between the attacking corrosive medium (blood and/or plasma) and, on the other hand, there is not an excessively great impairment in the shapability (important in stent dilatation). Thus, in the case when the layer thickness is too great, the layer would flake off in some areas during crimping or dilatation, so the layers underneath and the metallic base material would come in direct contact with the corrosive media. This would then result in accelerated corrosion.

As already described above, the first layer has pores, whereby a hydroxide of the metallic material(s) of the implant body is preferably formed as a third layer at the base of the pore, in particular in treatment of the implant in a sodium hydroxide solution as described above.

The first layer preferably contains at least one compound selected from the group comprising phosphates, oxides and hydroxides of the biodegradable material(s), strontium carbonate, strontium phosphate.

The inventive methods are explained below on the basis of examples and figures, whereby all the features illustrated and/or described here constitute the subject of the invention, regardless of how they are combined in the claims or their reference back to preceding claims.

EXAMPLES

Example 1

First a stent with a body consisting of a magnesium alloy, preferably WE43 (93 wt % magnesium, 4 wt % yttrium (W) and 3 wt % rare earth metals (E) not including yttrium) is made available.

Then the aqueous solution (electrolyte) is prepared by first pouring 500 mL distilled $H_2O$ into a glass beaker. Then the components of the aqueous solution are added in the order given below. It should be noted that the next following component may be added only after the preceding components have completely dissolved. The electrolyte is to be stirred constantly during this addition, which can be implemented with a magnetic stirrer (500 $min^{-1}$), for example. The components should also be added slowly to prevent excessive evolution of heat. The electrolyte synthesis may preferably take place in a double-walled coolable container. The following components may be added (all the following percentage amounts are percent by weight (wt %)):
1. 100 mL/L ethylenediamine solution (99%),
   100 g/L potassium dihydrogen phosphate,
   90 g/L strontium hydroxide octahydrate and
   40 mL/L aqueous ammonium hydroxide solution (25%)
or
2. 50 mL/L ethylenediamine solution (99%),
   50 g/L potassium dihydrogen phosphate,
   90 g/L strontium nitrate and
   20 mL/L aqueous ammonium hydroxide solution (25%) or
   25 g/L sodium hydroxide.

After completing one of the two batches identified as 1 or 2, the plasma-chemical coating process is performed.

Before the plasma-chemical coating process, a multistage degreasing in solutions containing surfactant, then rinsing in distilled $H_2O$ may be performed, if necessary, depending on the contamination status of the implant body.

Before the start of the plasma-chemical coating process, the body of the implant is connected to the anode of electrodes by means of a titanium wire or an aluminum wire in a method that ensures reliable electric contact. The counter-electrode (cathode) is made of an acid-resistant stainless steel. The anode and cathode of the electrodes are connected to a voltage source capable of delivering a pulsed voltage. The current density is about 10 $mA/cm^2$ at a frequency of at least 1 kHz.

After immersing the implant body in the aqueous solution, a constantly increasing pulsed bath voltage is applied. On reaching the bath voltage range of more than 100 V, which is characteristic of the treatment of magnesium alloys in the electrolyte composition, plasma-chemical surface effects occur, producing surface layers consisting of oxides, hydroxides and phosphates of the metallic base material of the implant body as well as other compounds recruited from the elements of the electrolyte. In particular because of the presence of the $Sr^{2-}$ ion, strontium carbonate is also formed from the carbon of ethylenediamine, the oxygen of the aqueous electrolyte and the strontium of the strontium hydroxide and/or strontium nitrate. Furthermore, strontium phosphate, which is a plasma-chemical conversion product of potassium dihydrogen phosphate and water, is also formed.

After reaching the final coating voltage of about 250 V, the current density previously set drops from about 10 $mA/cm^2$ to about 6 $mA/cm^2$. When this value is reached, the current supply is interrupted and the plasma-chemical process is terminated. The layer thickness of the first layer produced in this way preferably amounts to about 1 µm to about 20 µm, especially preferably between 2 µm and 8 µm. and depends essentially on the bath voltage used.

Then there is a multistep rinsing of the implant body in distilled water, separation of the implant from the contact wire and drying of the body of the implant in a circulating air oven at about 100° C.

By means of the plasma-chemical coating process described here, it is possible to produce implants which degrade within a desired time window. The degradation can surprisingly be controlled by a layer designed to be porous.

Example 2

This example describes the coating of nonresorbable implants of nitinol, stainless steel or cobalt-chromium alloys or degradable materials with a second layer 20 of metals, containing at least one element from the group of tantalum, niobium, zinc, iron and aluminum. The implant is first produced with known technologies such as laser cutting, electropolishing, etc., forming a body 5 (see FIG. 1). Then the surface of the body 5 is coated with tantalum, niobium, zinc, iron, aluminum or an alloy containing these metals. The coating technologies used may include ionic liquids, sputtering, high-rate atomization or vaporization.

Figure 1:
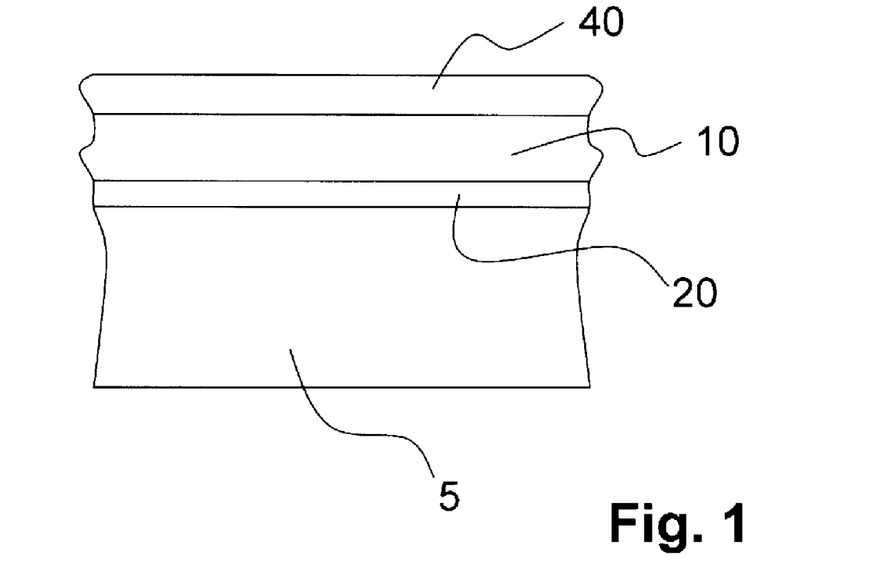
FIG. 1 shows a cross section through the layer structure of one exemplary embodiment of the inventive implant produced according to Example 2.

The second layer 20 is preferably produced with tantalum on a nitinol implant by means of an ionic liquid 1-butyl-1-methylpyrrolidiniumbis(trifluoromethylsulfonyl)amide from $TaF_5$, forming a tantalum layer 20 that is 0.5 µm to 1 µm thick, adhering securely due to anodic preoxidation of nitinol in the ionic fluid, so that it is difficult to remove mechanically.

In another exemplary embodiment, a magnesium implant whose body 5 consists of a magnesium alloy may be coated with nanocrystalline aluminum in the ionic fluid of $AlCl_3$ described above to form a second layer 20 containing nanocrystalline aluminum.

The resulting second layer 20 has a thickness in the range of a few micrometers. The layer thickness range to be set is preferably between 0.5 and 15 µm. Especially desirable coating parameters lead to a uniform layer thickness distribution of the second layer 20 even on the inside and/or in gaps and undercuts on the implant where access is difficult.

After producing the second layer 20, the implants are electrically connected to a thin wire of the same type (e.g., Ta or Nb) or to a wire of Ti or Al, then immersed in an aqueous electrolyte solution and contacted anodically. In the contacting, it is important to be sure that the contact pressure does not damage the layer material and that there is no electric contact with the base material.

The aqueous solution contains 100 mL/L ethylenediamine (99%), 50 g/L potassium dihydrogen phosphate, 10 g/L, sodium carbonate and 25 mL/L 25% aqueous ammonia solution (percentage amounts given in percent by weight (wt %)). The composition of the stated electrolyte solution is selected so that elements or compounds contained therein are recovered on the surface of the implant after a plasma-chemical coating process to be performed subsequently. The electrolyte solution is in a suitable container made of glass or plastic which also contains the counter-electrode, which is made of acid-resistant stainless steel and assumes the function of the cathode here.

After applying a steadily increasing pulsed anodic bath voltage with a frequency of at least 1 kHz to the implant, characterized by long pulse pauses, the layer material Ta and/or niobium is oxidized, and phosphates of these metals are also formed, so that the first layer 10 is formed on the surface of the second layer 20. Before the coating operation, it must be pointed out that the layer materials of the second layer 20 cover the implant on all sides (i.e., there are no defects) and the inventive electrolyte (in which the plasma-chemical effects occur) does not come in contact with the respective base material of the body 5 at all.

The composite layer 20 formed by these plasma-chemical effects has a porous surface due to the process. The pores have a statistical but relatively regular distribution and have an average pore diameter of about 1 to 3 µm. The layer is characterized by a high adhesion to the respective base material (nitinol, stainless steel, magnesium and/or cobalt-chromium alloys). The thickness and surface roughness of the inventive surface layer can be influenced through the process parameters described in the following examples. For example, depending on the application case, it is possible to produce a relatively smooth surface resembling a glass or ceramic and having predominantly worm-type pores or to produce a relatively rough surface with a crater-like surface morphology mixed with round pores. The final electrolyte voltages, which are specific for the metals tantalum and niobium and are in the range between 250 V and 450 V (depending on the layer thickness and surface roughness to be established), should not be exceeded. On the other hand, the plasma-chemical oxidation effects would reach the respective base material, depending on the thickness of the layer material originally applied.

The arc phenomena occurring in this case would lead to destruction of the composite layer structure just created. Again for this reason, the plasma-chemical process parameters are to be selected, so that there is depth oxidation of the material of the second layer 20 is not complete. The oxidation should at most proceed to a depth of the material which is 1 µm smaller than the original thickness of the second layer 20. Thus, a permanent metallic layer material thickness of the second layer 20 of about 1 µm is ensured, so that in the subsequent use case, it will assume most of the plastic deformation (e.g., in stent dilatation). It should be noted here that high-purity Ta and/or Nb is preferably applied because only high-purity elements have the plastification capacity required for the present application.

After reaching the optimum final voltage set for the respective layer system before the start of the process, the current density drops from about 1 A/dm$^2$ to about 50% of the initial value. After reaching this level, the process is interrupted by cutting off the power supply, and then the implant, which has been provided with the second layer 20 and the first layer 10, may be removed from the electrolyte. Rinsing is then performed immediately in multiple steps in hot distilled water at about 80° C. The rinsing serves to completely remove the residual electrolyte still adsorbed on and/or chemisorbed in the surface roughness. Ultimately the implant is dried in a drying cabinet at about 100° C.

After these process steps, a variety of further treatments may be used, depending on the intended application of the implant. These treatments may include immersion or spraying of polymer solutions to produce a fourth layer 40 arranged on the first layer 10 and containing active pharmaceutical components (e.g., for vascular intervention). A layer containing parylene is preferably applied as the fourth layer 40 (see Example 6). Solutions based on degradable or nondegradable polymers may be used to produce the fourth layer 40. The choice of active pharmaceutical substance(s) is made according to the respective application case. However, the fourth layer may also be omitted.

Example 3

Like Example 2, which is incorporated herein.
After drying in a drying cabinet, instead of dipping the implant in or spraying it with polymer solutions as the first layer, the implant is dipped in aqueous or nonaqueous media in which bone morphogenetic proteins (BMPs) are dissolved, the latter being drawn into the pore structure by applying a vacuum, then remaining there after the drying process. so they have a positive influence on bone growth in the case of orthopedic implants.

Example 4

Like Example 2, which is incorporated herein.
After drying in a drying cabinet, the implants are dipped in dilute hyaluronic acid, which accelerates cartilage production in the case of articular implants.

Example 5

Like Example 2, which is incorporated herein.
After drying in a drying cabinet, the implants are dipped in solutions containing magnesium stearate (mixture of isopropanol and magnesium stearate) to produce another alternative fourth layer. The surface containing magnesium stearate, which is formed after drying, minimizes the coefficient of friction in the catheter and thus facilitates the release of stents, for example, at the implantation site.

Example 6

Like Example 2, which is incorporated herein.
After drying in the drying cabinet, the implants are coated with parylene as an alternative fourth layer by means of plasma polymerization. The layer thicknesses of the parylene layer (of the type C, N or D) may be between about 0.5 µm and about 10 µm, preferably between about 0.5 µm and about 7 µm. With such a layer combination, the degradation stability of the endoprosthesis is increased again significantly and the coefficient of friction in the catheter is minimized.

Example 7

Like Example 2 which is incorporated herein.
Then to produce another alternative fourth layer, a coating is prepared with a nonresorbable polymer containing powder particles of barium (pure substance), bismuth or tungsten or their carbides. Using this coating, a further increase in radiopacity of the endoprosthesis is made possible.

Example 8

Figure 2:
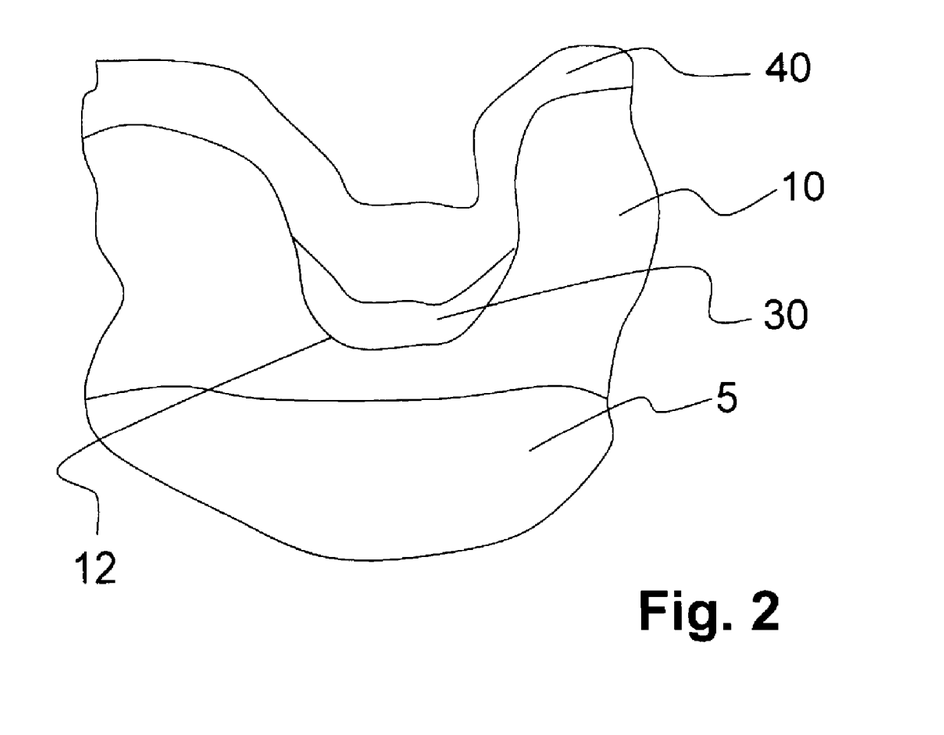
FIG. 2 shows a cross section through a detail of the layer structure of another exemplary embodiment of the inventive implant produced according to Example 8, in particular a cross section through a pore of the first layer.

In the preceding examples, in addition to the other steps, an aftertreatment with a strongly basic aqueous sodium hydroxide solution may be performed to produce the third layer 30, which is arranged essentially in the base of the pores (see FIG. 2), immediately after the plasma-chemical coating to produce the first layer 10, but the second layer 20 may also be omitted, as shown in FIG. 2. In the aftertreatment, the reaction container is treated with ultrasound, while at the same time, argon or nitrogen is blown in through a frit. This also permits a chemical interaction to take place at the base 12 of the pores, which is difficult to access. This process forms a third layer 30 in the base 12 of the pores, this layer being several tens of nm thick and having the effect of a diffusion barrier and/or being advantageous under mechanical stress. This barrier effect can be further increased if an oxygen plasma is used after an intermediate drying process. in the case of an implant treated in this way. This oxygen plasma causes a complete or partial conversion (depending on the treatment time) of the hydroxide of the base material contained in the third layer 30 to the oxide of the base material (e.g., conversion of magnesium hydroxide to magnesium oxide), in particular in the upper area of the third layer 30.

In another preferred example, plasma polymerization with a biocompatible polymer, preferably with parylene N, is performed in the same coating installation to produce the fourth layer 40. A parylene N layer 40 approximately 0.5 to 7 μm thick covers the implant. Due to the great ability to permeate into gaps, the polymer again penetrates deeply into the pores down to the base of the pores.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NUMERALS

5 body of the implant
10 first layer
12 base of a pore in the first layer 10
20 second layer
30 third layer
40 fourth layer

What is claimed is:

1. A method for manufacturing an implant, comprising an endoprosthesis, having a body comprising a metallic material, the method comprising the following steps:
   a) preparing the body of the implant,
   b) plasma-chemical treatment of at least a portion of a surface of the body in an aqueous solution by applying a plasma-generating alternating voltage to the body of the implant, the voltage having a frequency of at least approximately 1 kHz, for creating a porous layer on the portion of the surface of the body that is to be treated, and
   c) performing an aftertreatment to seal the base of the pores without sealing the entirety of the pores to preserve an exposed roughened surface.

2. The method according to claim 1, wherein the body comprises at least one metallic material that is biodegradable.

3. The method according to claim 2, wherein the aqueous solution contains one or more $Sr^{2-}$ ions, optionally at a concentration of 0.05 mol/L to 2.0 mol/L $Sr^{2-}$.

4. The method according to claim 1, further comprising before the step of plasma chemical treatment, applying a layer containing at least one element selected from the group consisting of tantalum, niobium, zinc, iron and aluminum to at least a portion of the surface of the body by means of an ionic fluid, by sputtering, high-rate atomization and/or vaporization.

5. The method according to claim 1, wherein the porous layer is rinsed in a solvent, optionally with distilled $H_2O$ and then is dried in a circulating oven at a temperature of at least 80° C.

6. The method according to claim 1, wherein the aqueous solution comprises one or more ions selected from the group consisting of phosphates, carbonates and silicates.

7. The method according to claim 1, wherein the aqueous solution comprises at least one member selected from the group consisting of a buffer, potassium dihydrogen phosphate and sodium dihydrogen phosphate.

8. The method according to claim 1, wherein the surface of the body is treated electrochemically before the plasma-chemical treatment.

9. The method according to claim 1, wherein the plasma-chemical treatment of the surface of the body is performed by applying a pulsed voltage to the body, its amplitude exceeding at least approximately 90 V for most of the treatment period and the current density in the plasma-chemical treatment is at least 8 $mA/cm^2$.

10. The method according to claim 1, further comprising applying a polymer layer to the body of the implant after performing the aftertreatment, wherein the polymer optionally comprises parylene.

11. The method according to claim 1, wherein the step of performing the aftertreatment comprises treating the body in a strong base.

12. The method according to claim 1, further comprising applying a radiopaque layer to the body of the implant.

13. The method according to claim 1, wherein the endoprosthesis is a stent.

14. A method for manufacturing an implant, comprising an endoprosthesis having a body comprising a metallic material, the method comprising the following steps:
   a) preparing the body of the implant,
   b) applying a layer containing at least one element selected from the group consisting of tantalum, niobium, zinc, iron and aluminum to at least a portion of a surface of the body by means of an ionic fluid containing pyrrolidinium ions, and
   c) plasma-chemical treatment of at least a portion of a surface of the body in an aqueous solution by applying a plasma-generating alternating voltage to the body of the implant, the voltage having a frequency of at least approximately 1 kHz, for creating a porous layer on the portion of the surface of the body that is to be treated.

15. The method according to claim 14, wherein the aqueous solution comprises one or more ions selected from the group consisting of phosphates, carbonates and silicates.

16. The method of claim 14, further comprising applying a polymer layer to the body of the implant after the plasma-chemical treatment, wherein the polymer optionally comprises parylene.

17. The method according to claim 14, wherein the endoprosthesis is a stent.

18. A method for manufacturing an implant, comprising an endoprosthesis, having a body comprising a metallic material, the method comprising the following steps:
  a) preparing the body of the implant,
  b) plasma-chemical treatment of at least a portion of a surface of the body in an aqueous solution by applying a plasma-generation alternating voltage to the body of the implant, the voltage having a frequency of at least approximately 1 kHz, for creating a porous layer on the portion of the surface of the body that is to be treated, and
  c) performing an aftertreatment of the body of the implant in an aqueous, strongly basic sodium hydroxide solution and with the action of ultrasound and/or injection of argon and/or nitrogen to create a sealing layer.

19. The method according to claim 18, further comprising applying a radiopaque layer to the body of the implant.

20. The method according to claim 18, further comprising applying a polymer layer to the body of the implant after performing the aftertreatment, wherein the polymer layer optionally comprises parylene.

* * * * *